US008685747B2

(12) United States Patent
Zenhausern et al.

(10) Patent No.: US 8,685,747 B2
(45) Date of Patent: Apr. 1, 2014

(54) POROUS MATERIALS FOR BIOLOGICAL SAMPLE COLLECTION

(75) Inventors: Frederic Zenhausern, Fountain Hills, AZ (US); Ralf Lenigk, Chandler, AZ (US); James Kinder, Bellevue, WA (US); Jianing Yang, Tempe, AZ (US)

(73) Assignee: Arizona Board of Regents, A body corporate of the State of Arizona Acting for and on Behalf of Arizona State University, Scottsdale, AZ (US)

( * ) Notice: Subject to any disclaimer, the term of this patent is extended or adjusted under 35 U.S.C. 154(b) by 394 days.

(21) Appl. No.: 13/121,031

(22) PCT Filed: Aug. 14, 2009

(86) PCT No.: PCT/US2009/053944
§ 371 (c)(1),
(2), (4) Date: Sep. 28, 2011

(87) PCT Pub. No.: WO2010/019920
PCT Pub. Date: Feb. 18, 2010

(65) Prior Publication Data
US 2012/0034601 A1     Feb. 9, 2012

Related U.S. Application Data

(60) Provisional application No. 61/089,444, filed on Aug. 15, 2008.

(51) Int. Cl.
*C12Q 1/68* (2006.01)
*G01N 33/50* (2006.01)

(52) U.S. Cl.
USPC ........... 436/174; 436/177; 436/178; 436/808; 436/86; 436/94; 422/68.1; 422/527; 435/6.1; 435/283.1

(58) Field of Classification Search
USPC .................... 436/174, 177, 178, 808, 86, 94; 422/68.1, 527; 435/6.1, 283.1
See application file for complete search history.

(56) References Cited

U.S. PATENT DOCUMENTS

| 6,184,011 B1 | 2/2001 | Siegel et al. |
| 6,447,991 B1 | 9/2002 | Daitch et al. |

(Continued)

FOREIGN PATENT DOCUMENTS

| EP | 0707474 | 8/2000 |
| WO | WO2005079531 | 9/2005 |

OTHER PUBLICATIONS

PCT/US2009/053944 International Search Report and Written Opinion, 12 pages, Mar. 22, 2010.

(Continued)

*Primary Examiner* — Monique Cole
(74) *Attorney, Agent, or Firm* — Novak Druce Connolly Bove + Quigg LLP; Amy A. Dobbelaere

(57) ABSTRACT

Methods, apparatuses, and systems for collecting samples using hybrid porous materials that include an organic material and an inorganic material. A method for sample collection includes contacting a hybrid porous material and a biological sample to the porous material. The hybrid porous material includes an inorganic material and an organic material. The method includes placing the porous material with the attached sample in a liquid medium, wherein the sample is separated from the porous material in the liquid medium to form a separated sample, and collecting the separated sample in the medium.

44 Claims, 6 Drawing Sheets

(56) References Cited

U.S. PATENT DOCUMENTS

| | | | |
|---|---|---|---|
| 2001/0049148 | A1 | 12/2001 | Wolk et al. |
| 2002/0094531 | A1 | 7/2002 | Zenhausern |
| 2004/0132846 | A1 | 7/2004 | Leventis et al. |
| 2004/0224362 | A1 | 11/2004 | Gjerde et al. |
| 2005/0153346 | A1 | 7/2005 | Schneider |
| 2006/0199945 | A1 | 9/2006 | Gjerde |
| 2006/0264133 | A1 | 11/2006 | Krajewski et al. |
| 2008/0070274 | A1 | 3/2008 | Lee et al. |
| 2012/0034601 | A1* | 2/2012 | Zenhausern et al. ............ 435/6.1 |

OTHER PUBLICATIONS

PCT/US2009/053944 International Preliminary Report on Patentability, 6 pages, Feb. 15, 2011.

Gadre et al. "Hybrid Nanomaterial Scaffolds for Specific Biomedical Applications" Materials Research Society, Mater. Res. Soc. Symp. Proc. vol. 1237, 2010, 1237-TT05-02, 6 pages.

Pierre et al. "Chemistry of Aerogels and Their Applications" Chem. Rev. 2002, 102, pp. 4243-4265.

Whatman® Brochure "Innovative Solutions for Forensic DNA Collection, Archiving and Purification" 8 pages, Apr. 2004, http://www.whatman.com/UserFiles/File/Brochures/Bioscience/Innovative%20Solutions%20for%20Forensics.pdf.

Voorhees et al. "Enhanced Elution of Sperm from Cotton Swabs Via Enzymatic Digestion for Rape Kit Analysis" J Forensic Sci, May 2006, vol. 51, No. 3, pp. 574-579.

Zhang et al. "Isocyanate-crosslinked silica aerogel monoliths: preparation and characterization" Journal of Non-Crystalline Solids 350 (2004) pp. 152-164.

Leventis et al. "Polymer nano-encapsulation of templated mesoporous silica monoliths with improved mechanical properties" Journal of Non-Crystalline Solids 354 (2008) pp. 632-644.

"Polymer Cross-Linked Aerogels (X-Aerogels)" National Aeronautics and Space Administration, LEW-17685-1, Sep. 25, 2008, 2 pages, https://technology.grc.nasa.gov/support/images/GR-0013_LEW-17685(online).pdf.

Zhang "Beyond the Petri dish" Nature Biotechnology vol. 22, No. 2, Feb. 2004, pp. 151-152.

Griffith et al. "Capturing complex 3D tissue physiology in vitro" Nature Reviews, Molecular Cell Biology vol. 7, Mar. 2006, pp. 211-224.

Lowman et al. "Structural and Dynamic Response of Neutral and Intelligent Networks in Biomedical Environments" Advances in Chemical Engineering, vol. 29, 2004, pp. 75-130, ISSN 0065 2377.

Zhang et al. "Designer self-assembling peptide nanofiber scaffolds for 3D tissue cell cultures" Seminars in Cancer Biology 15 (2005) pp. 413-420.

"Global Expansion of Forensic DNA" Needham Growth Conference, Jan. 11, 2007, Applied Biosystems, 1 page.

Kanamori et al. "Elastic organic—inorganic hybrid aerogels and xerogels" J Sol-Gel Sci Technol (2008) 48: pp. 172-181.

Capadona et al. "Flexible, low-density polymer crosslinked silica aerogels" Polymer 47 (2006) pp. 5754-5761.

Murugan et al. "Design Strategies of Tissue Engineering Scaffolds with Controlled Fiber Orientation" Tissue Engineering vol. 13, No. 8, 2007, pp. 1845-1866.

* cited by examiner

300

Bringing a hybrid composite in contact with a biological sample to attach the biological sample to the aerogel — 305

Place the hybrid composite with the attached sample in a liquid medium to separate the sample from the hybrid composite — 310

Collect the separated sample — 315

FIG. 3

POROUS MATERIALS FOR BIOLOGICAL SAMPLE COLLECTION

CROSS REFERENCE TO RELATED APPLICATIONS

This application is a U.S. National Phase Application under 35 U.S.C. §371 of International Application PCT/US2009/053944, filed on Aug. 14, 2009, which claims priority to U.S. Provisional Patent Application No. 61/089,444, entitled Porous Materials for Biological Sample Collection, which was filed on Aug. 15, 2008; the entire contents of each of the foregoing are hereby incorporated by reference.

TECHNICAL FIELD

This patent document relates to biological sample collection.

BACKGROUND

DNA can be found in bodily fluids, such as saliva, as well as in other parts of the body including hair, skin, and the like. Identification based on DNA includes collecting the biological samples containing DNA, processing the samples to obtain a profile of the DNA in the sample, and comparing the obtained profile against a reference profile. Biological samples that contain DNA can be found under controlled conditions, for example, in a laboratory, and in uncontrolled environments, for example, crime scenes. One example of collecting biological samples includes adhering the sample to a cotton swab. An example of processing samples can include lysis to access the DNA in the sample, DNA amplification by methods such as polymerase chain reaction (PCR), electrophoretic separation, and detection using techniques including optical techniques, electrochemical techniques, and the like.

SUMMARY

In one example, implementations of a method for collecting biological samples using inorganic-organic hybrid composites are described. The hybrid composite can be formed by attaching a layer of organic material on a functionalized surface of an inorganic substrate to form the hybrid composite. For example, a polysiloxane network can be formed by the condensation of an alkoxy silane followed by the attachment of the organic polymer layer by the polymerization of monomers to the functionality of the silane surface. The method for collecting biological samples can include attaching a biological sample to the hybrid composite, placing the hybrid composite with the attached sample in a liquid medium, separating the sample from the hybrid composite, and collecting the sample in the liquid medium. The properties of the hybrid composite can be configured to enable attaching the sample to the hybrid composite, while the properties of the liquid medium can be configured to enable separating the sample from the composite.

In general, one innovative aspect described in this document can be embodied in methods for sample collection that include contacting a hybrid porous material and a biological sample to the porous material. The hybrid porous material includes an inorganic material and an organic material. The method further includes placing the porous material with the attached sample in a liquid medium. The sample is separated from the porous material in the liquid medium to form a separated sample. The method also includes collecting the separated sample in the medium.

This, and other aspects, can include one or more of the following features. The biological sample can include deoxyribonucleic acid. Placing the porous material with the attached sample in a liquid medium can cause the porous material to dissolve in the liquid medium, thereby separating the sample. The hybrid porous material includes a silane component, an alkoxy silane component, and an organic polymer component. The hybrid porous material can consist of a silane component and an organic polymer component. The organic polymer component can be attached to the surface of the inorganic organic hybrid composite material. The method can further include entrapping the biological sample in a porous structure of the porous material. The method can also include processing the porous material to chemically activate a surface of the porous material. Contacting the porous material and the biological sample can further include causing the biological sample to chemically adhere to the chemically activated surface. Contacting the porous material and the biological sample can further include placing the porous material on the biological sample. Contacting the porous material and the biological sample can further include swiping the porous material against the biological sample.

Another innovative aspect described in this document can be embodied in methods including attaching an inorganic material and an organic material, wherein a biological sample is attachable to the inorganic material and the attached organic material; and collecting the biological sample with the inorganic material.

This, and other aspects, can include one or more of the following features. Collecting the biological sample with the inorganic material can include attaching the biological sample to the inorganic material, placing the inorganic material with the attached biological sample in a liquid medium to separate the biological sample from the surface, and collecting the separated biological sample in the liquid medium. The biological sample can be attached to a surface of the inorganic material. The biological sample can be absorbed into an interior of the inorganic material. Preparing the inorganic material to attach to the organic material can include preparing the inorganic material by mixing a quantity of a silane, a quantity of an alkoxy silane, and a quantity of a solution, wherein the alkoxy silane prepares the inorganic material to attach to the organic material. The siloxane can be tetramethylorthosilicate (TMOS). The solution can include at least one of an alcohol and water. The alcohol can be methanol. The solution can include alcohol and water in a weight/volume ratio. The alkoxy silane can be allyltrimethoxysilane. The organic material can be polymethylmethacrylate (PMMA), wherein the PMMA is formed by polymerization of methyl methacrylate (MMA), and wherein the PMMA grows on the surface of the first material.

Another innovative aspect described in this document can be embodied in a system including a hybrid porous material including an inorganic material and an organic material, the hybrid porous material including a surface attachable to a biological sample, and a liquid medium in which the biological sample separates from the surface.

This, and other aspects, can include one or more of the following features. The hybrid porous material can include a silane component, an alkoxy silane component, and an organic polymer component. The hybrid porous material can be prepared by mixing a known quantity of the siloxane component, a known quantity of the alkoxy silane component, and a known quantity of a solution. The silane component can be tetramethylorthosilicate (TMOS). The solution can include at least one of an alcohol and water. The alcohol can be methanol.

Another innovative aspect described in this document can be embodied in a method of manufacturing a hybrid composite, the method comprising adding an alkoxy silane to a precursor including a metal oxide to cause hydrolysis and condensation reactions, adding a polymerization solution to the alkoxy silane and the precursor to cause a polymerization reaction to form a porous inorganic material, and adding an organic functional component to the porous inorganic material wherein the organic component polymerizes and attaches to the porous inorganic material to form a hybrid composite, wherein the alkoxy silane, the precursor, the polymerization solution, and the organic functional component are selected such that a biological sample, when contacted by the hybrid composite, attaches to the hybrid composite.

This, and other aspects, can include one or more of the following features. The metal oxide is based on one of silica, aluminum, vanadium, and ruthenium. The alkoxy silane is one of or a mixture of allyltrimethoxysilane, tetraethylorthosilicate, or tetramethylorthosilicate. The polymerization solution includes an alcohol. The polymerization solution additionally includes water. The alcohol is one of methanol and ethanol. The method further includes adding a catalyst to increase a rate of polymerization, the catalyst including one or hydrochloric acid, nitric acid, and sodium hydroxide. The organic functional component is methylmethacrylate. The method further includes attaching the hybrid composite to a rod.

Still another innovative aspect of this invention can be implemented in an apparatus including a hybrid porous material including an inorganic material and an organic material, the hybrid porous material manufactured using an alkoxy silane, a precursor having a metal oxide mixed with the alkoxy silane, a polymerization solution to polymerize the alkoxy silane mixed with the precursor, and an organic functional component included in the organic material, wherein the alkoxy silane, the precursor, the polymerization solution, and the organic functional component are selected such that a biological sample, when contacted by the hybrid porous material, attaches to the hybrid porous material, and a rod having an end attached to the hybrid porous material, wherein the porous material attached to the rod is swiped against the biological material so that the hybrid porous material contacts the biological sample.

This, and other aspects, can include one or more of the following features. The alkoxy silane is tetramethylorthosilicate (TMOS). The polymerization solution comprises at least one of an alcohol and water. The alcohol is methanol.

Still another innovative aspect described in this document can be implemented in a hybrid composite material manufactured by a method comprising adding an alkoxy silane to a precursor including a metal oxide to cause hydrolysis and condensation reactions, adding a polymerization solution to the alkoxy silane and the precursor to cause a polymerization reaction to form a porous inorganic material, and adding an organic functional component to the porous inorganic material wherein the organic component polymerizes and attaches to the porous inorganic material to form the hybrid composite, wherein the alkoxy silane, the precursor, the polymerization solution, and the organic functional component are selected such that a biological sample, when contacted by the hybrid composite, attaches to the hybrid composite. The metal oxide is based on one of silica, aluminum, vanadium, and ruthenium. The alkoxy silane is one of or a mixture of allyltrimethoxysilane, tetraethylorthosilicate, or tetramethylorthosilicate.

Other innovative aspects described in this document can be embodied in a method for sample collection including bringing a porous material in contact with a biological sample to attach the biological sample to the porous material, placing the porous material with the attached sample in a liquid medium to separate the sample from the porous material, and collecting the separated sample in the medium. The biological sample comprises deoxyribonucleic acid. The porous material is an inorganic organic hybrid composite material which comprises a silane component, an alkoxy silane component, and an organic polymer component. The organic polymer component is attached to the surface of the inorganic organic hybrid composite material. The method further includes entrapping the biological sample in a porous structure of the porous material. The method further includes processing the porous material to chemically activate a surface of the porous material. Bringing the porous material in contact with the biological sample includes causing the biological sample to chemically adhere to the chemically activated surface. Bringing the porous material in contact with the biological sample includes placing the porous material on the biological sample. Bringing the porous material in contact with the biological sample comprises placing the biological sample on the porous material.

In another innovative aspect, a method includes preparing a first material by enabling a second material to attach to the first material, wherein the first material with the attached second material is configured to enable a biological sample to attach to the first material, and collecting the biological sample with the first material. Collecting the biological sample with the first material includes attaching the biological sample to the surface of the first material, placing the first material with the attached biological sample in a liquid medium to separate the biological sample from the surface, and collecting the separated biological sample in the liquid medium. Enabling the second material to attach to the first material includes preparing the first material by mixing a known quantity of a silane, a known quantity of an alkoxy silane, and a known quantity of a solution, wherein the alkoxy silane enables the second material to attach to the surface of the first material. The siloxane is tetramethylorthosilicate (TMOS). The solution includes at least one of an alcohol and water. The alcohol is methanol. The solution includes alcohol and water in a weight/volume ratio. The alkoxy silane is allyltrimethoxysilane. The second material is polymethylmethacrylate (PMMA), wherein the PMMA is formed by polymerization of methyl methacrylate (MMA), and wherein the PMMA grows on the surface of the first material.

In another innovative aspect, a system includes a porous material configured to enable a biological sample to attach to a surface of the porous material, and a liquid medium configured to enable separating the biological sample from the surface. The porous material is an inorganic organic hybrid composite material comprising a silane component, an alkoxy silane component, and an organic polymer component. The porous material is prepared by mixing a known quantity of the siloxane component, a known quantity of the alkoxy silane component, and a known quantity of a solution. The silane component is tetramethylorthosilicate (TMOS). The solution includes at least one of an alcohol and water. The alcohol is methanol. The solution includes alcohol and water in a weight/volume ratio. The alkoxy silane component is allyltrimethoxysilane. The organic polymer component is polymethylmethacrylate.

Particular implementations of the subject matter described in this specification can be implemented to realize one or more of the following potential advantages. The structure of the hybrid composite can be tailored to alter the porosity, surface area, and other properties of the composite. The ability to alter the choice of the inorganic and the organic portions of the hybrid composite based on the desired structure of the resulting composite and the desired function to which the hybrid composite is applied can enable applying the hybrid composite for the collection of several biological samples. Further, the ability to alter the functionalizing groups in the inorganic substrate based on the polymeric material to be attached to the surface of the hybrid composite can enable attaching different polymeric materials to the surface. The choice of the polymeric material, in turn, can be based on the desired application of the composite. Furthermore, the functionalized surface of the inorganic substrate can ease the attachment of the polymer on the surface of the hybrid composite. Also, the porous network of the resulting hybrid composite can increase the quantity of sample collected. In addition, the properties of the liquid medium to separate the sample from the hybrid composite can be configured such that the quantity of sample separated from the hybrid composite relative to the quantity adhered to the hybrid composite is high. In this manner, the efficiency of sample collection can be increased. The shape of the hybrid composite can also be manipulated to suit any sample collection system or device.

The details of one or more implementations of the specification are set forth in the accompanying drawings, the description, and the claims.

BRIEF DESCRIPTION OF THE DRAWINGS

FIG. 3 is a flow chart of an example of a process for collecting samples.

Like reference numbers and designations in the various drawings indicate like elements.

DETAILED DESCRIPTION

Hybrid composites can be formed by the inclusion of organic groups to inorganic substrates. The choice of organic groups can vary the properties, including the surface properties, of the resulting hybrid composite. For example, in hybrid composites that have an inorganic porous network, the choice of the inorganic material can provide functional properties to the porous network, including the surface. Such functional properties can enable attaching organic groups, for example, monomers, to the surface. Polymerization of the monomers on the surface of the hybrid composites can provide the resulting hybrid composite with properties that enable using the combination of a hybrid composite and the polymeric surface in multiple applications. The properties and functions of the hybrid composite, for example, mechanical properties, porosity gradient, polymer functionalization, and the like, can be controlled.

Examples of controlling hybrid composite properties in specific applications can include controlling porosity gradient to allow differential cell sorting, polymer functionalization to allow selective molecular recognition and trapping of specific components of a biological sample, such as antigens-antibody (sperm cell sorting), and the like. The properties of the hybrid composite can be tailored, for example, to have high solubility and high surface area such that the efficiency of the application of such composites to collect and release biological samples is enhanced. Further, the properties can be tailored such that the hybrid composites provide a controlled microenvironment for preserving the integrity of the biological sample. For example, the moisture level of the hybrid composite can be tuned to a level necessary for the biological sample to survive.

Figure 1:
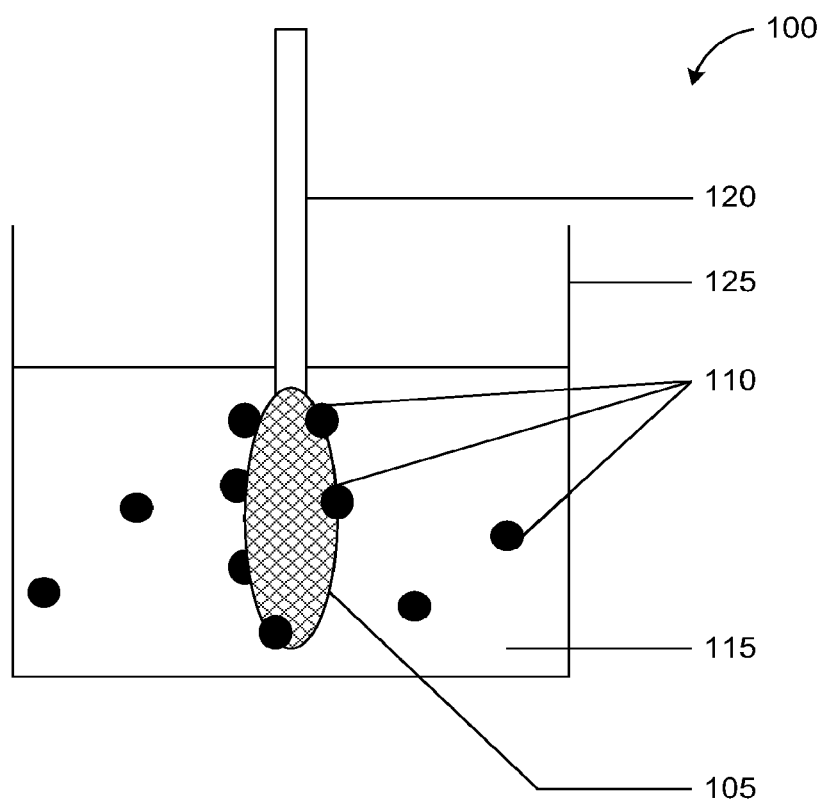
FIG. 1 is a schematic of an example of a system for collecting biological samples.
Figure 2:
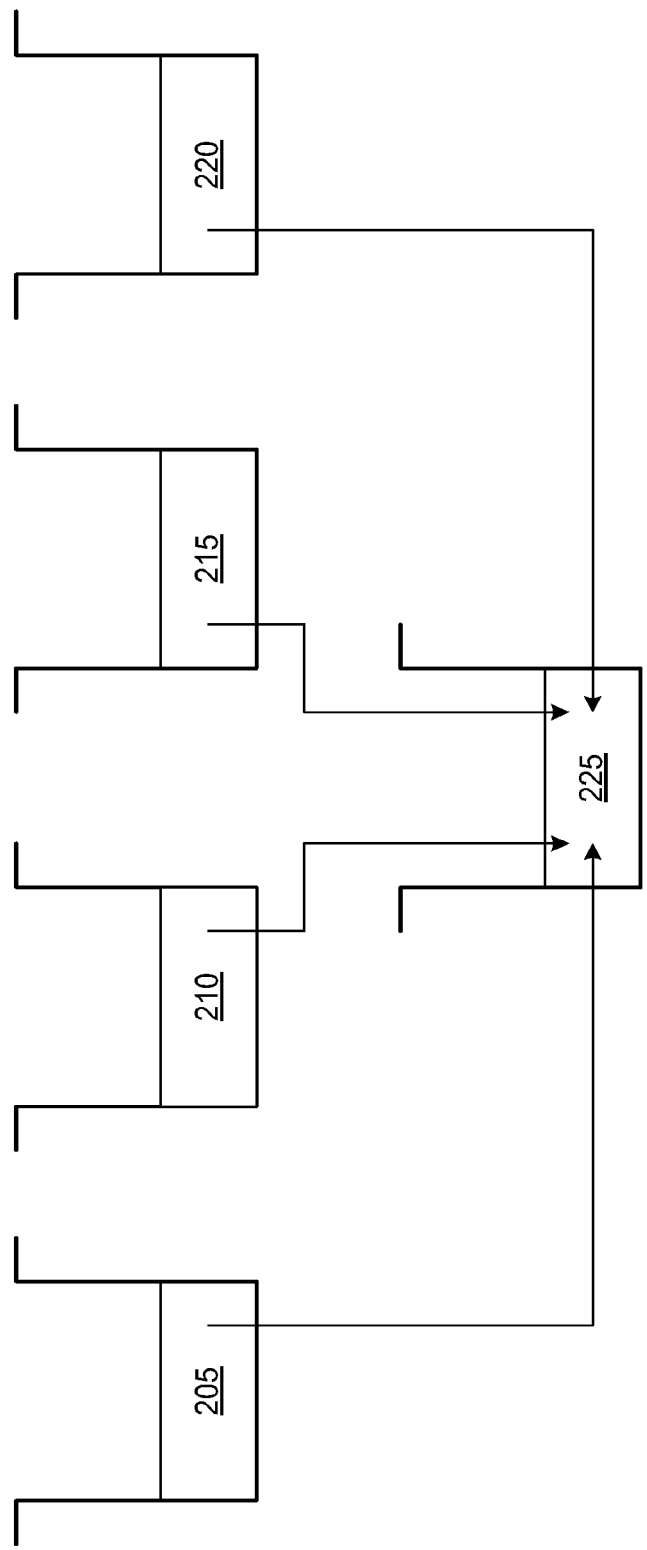
FIG. 2 is a schematic of an example of a process for making hybrid composites.

An example application of the hybrid composite for DNA collection is described with reference to FIG. 1. FIG. 1 is an example of a schematic of a system 100 for collecting biological samples. In some implementations, the system 100 can include an inorganic-organic hybrid composite 105 to which the biological samples 110 are attached. The hybrid composite 105 can be formed by the condensation of metal oxide. For example, a condensation reaction of an alkoxysilane can cause the formation of a polysiloxane network. Organic polymers can be attached to the polysiloxane network by polymerization of monomers such as methyl methacrylate, styrene, and the like, with functionality on the silanes, for example, amines, allyls, and the like. When the inorganic portion contains silica, then the hybrid composite 105 can be an Ormosil or an Ormocer.

The biological samples 110 can include cells, tissues, fluids, or any other materials containing materials of interest, such as DNA. When the hybrid composite 105 is placed against the sample 110, the samples 110 can be attached to the surface of the hybrid composite 105. For example, since the surface of the hybrid composite 105 is porous, the samples 110 can be entrapped in the pore structure of the hybrid composite 105. In implementations in which silica aerogels are used as hybrid composites, pore volume values, measured using Micromeritics Accelerated Surface Area and Porosity Analyzer® (Norcross, Ga.), was approximately 4 $cm^3$/g. Surface area analysis of silica aerogel composites measured using similar techniques was approximately 450 $cm^2$/g-500 $cm^2$/g. Further, skeletal density measurements for such composites was approximately 2.2 g/$cm^3$. Percentage porosity calculations based on the pore volume and skeletal density showed porosity to be approximately 90%. The hybrid composite 105 with the attached samples 110 can be placed in a liquid medium 115. The properties of the liquid medium 115 can be configured such that when the hybrid composite 105 is exposed to the liquid medium 115, the samples 110 are separated from the hybrid composite 105.

In some implementations, the hybrid composite 105 can be attached to a base 120, for example, the end of a rod, while the liquid medium 115 can be held in a container 125. In some scenarios, the biological sample 110 can be blood found at a crime scene. A user can collect the biological sample 110 using the base 120 with the attached hybrid composite 105 by swiping the surface of the hybrid composite 105 against the sample 110. The sample 110 can be attached to the hybrid composite 105 surface and can either be processed or transported to a desired location. A user can immerse the end of the base 120 containing the hybrid composite 105 with the attached sample 110 into the liquid medium 115 that is held in the container 125. Due to the properties of the liquid medium 115 and the hybrid composite 105, the sample 110 can be released from the surface of the hybrid composite 105 and into the medium 115. In this manner, the sample 110 can be retrieved from one location, collected, and subsequently prepared for processing.

FIG. 2 is an example of a process for making inorganic-organic hybrid composites 105. The hybrid composites 105 can be based on silica. For example, alkoxy silanes can be added to the hybrid composite 105 to provide surface functionalities which can enable growing polymers to enhance the properties of the hybrid composites 105. In some implementations, the alkoxy silanes can be allyltrimethoxysilane. Alternatively, the alkoxy silane can be allyltrimethoxysilane, 3-aminopropyltriethoxysilane, and the like. In some implementations, combinations of two or more alkoxy silanes can be included in the formulation for the hybrid composite 105. The inorganic portion can be based on elements including aluminum, vanadium, ruthenium, and the like. The hybrid composite 105 can be prepared by a process involving hydrolysis and condensation. In some implementations, the hybrid composite 105 can be silicon dioxide based precursors 205 to which alkoxy silanes 210, for example, allyltrimethoxysilane, can be added. The choice of alkoxy silane 210 is based on the desired surface functionality of the resulting hybrid composite 105. The hydrolysis step includes mixing a precursor 205 with an appropriate alkoxy silane 210.

In some implementations, the precursor 205 can be tetramethylorthosilicate (TMOS) including allyltrimethoxysilane to which a polymerization solution 215 can be added. In some implementations, tetraethylorthosilicate (TEOS) can be used as the precursor 205. The polymerization solution 215 can be a mixture of methanol and water in 50% weight/volume ratio. The polymerization solution 215 can be a mixture of ethanol and water, only ethanol, only methanol, other alcohols, and the like. Catalysts, such as acids or bases, can be used in the composite formation process to promote formation. For example, catalysts like hydrochloric acid (HCl), nitric acid ($HNO_3$), and sodium hydroxide ($NH_4OH$) can be used to enhance the gelation rate when TMOS and/or TEOS are used as precursor 205. In addition, initiators 220 can be added to serve as a catalyst during the polymerization process. For example, the diazo catalyst is a free radical catalyst that affects the olefin polymerization reaction. The addition of the precursor 205, the alkoxy silane 210, and the polymerization solution 215 can result in the formation of the porous inorganic portion of the hybrid composite with the alkoxy silane distributed through out the porous network, including the surface, of the hybrid composite.

In addition, the hybrid composite 105 preparation process can include the addition of functional chemicals 220 such as methylmethacrylate (MMA) monomer, subsequent to the gelation, to impart functional properties to the resultant hybrid composite. For example, the addition of MMA and the subsequent forming of a layer of polymer on the surface of the hybrid composite can increase the strength of the resultant hybrid composite, thereby providing structural rigidity, the ability to machine the hybrid composite, and the like. The MMA monomers can be polymerized to make (poly)MMA (PMMA). In some implementations, monomers such as MMA can be included in the hybrid composite formation process such that the resulting polymers can be grown on the surface of the hybrid composite, for example, by attaching the polymer to the inorganic portion, to impart strength to the hybrid composite. The strength of the hybrid composite can depend on the thickness of the polymer substrate on the surface, which, in turn, can depend on the quantity of monomer added during preparation of the hybrid composite. Other monomers such as dianhydrides, amines, and the like, can also be added in the hybrid composite preparation process preparation process to grow other types of polymers on the surface such as condensation polymers. The hybrid composite 105 can be prepared with or without the addition of functional chemicals 220.

In some implementations, the TMOS precursor 205, the alkoxy silane, for example, allyltrimethoxysilane, 210, the methanol/water polymerization solution 215, and the initiator 220 can be added in pre-determined quantities to form a gel solution 225. In some implementations, the ratio of components can be as follows: TMOS—20%, allypropyltrimethoxysilane—4%, MMA—4%, $H_2O$—11%, ammonium hydroxide ($NH_4OH$)—0.4%, methanol—60.1%, diazo initiator—0.4%. In addition, the porous structure of the hybrid composite 105 can be manipulated by including additional components to the gel solution. For example, by adding long chain polymers, such as polyethyleneoxide (PEO), polyethylene glycol (PEG), and the like, the pore structure of the resulting hybrid composite 105 can be altered. Such alteration can be accomplished by altering the quantity of polymer added to the gel solution 225, adding polymers of different molecular weights, or both. Alternatively, or in addition, pore structure can be altered by adding branched polymers, thermally degradable compounds that decompose after heat treatment, or combinations of both. Further, the addition of polymers can increase the structural strength of the resultant hybrid composite 105. Furthermore, to tailor pore size, expanding agents, for example, trimethyl benzene (TMB) and templating agents, for example, Pluronic F127 (BASF, Florham, N.J.). The tailorability of pore size can be studied using methods described in "Pore structure control of silica gels based on phase separation," (K. Nakanishi et al, Journal of Porous Materials, 1997) and "Polymer encapsulation of template silica monoliths," (N. Leventis et al, Journal of Non-Crystalline Solids, 2007).

In addition, the structural strength of the hybrid composite can be manipulated by including chemicals such as styrene, isocyanate, and the like in the polymerization solution 210. In some implementations, the hybrid composite 105 can be a cross-linked aerogel prepared by adding an appropriate alkoxy silane during the preparation process and, on the surface of which, an organic polymer layer can be attached. Details regarding methods and compositions for preparing cross-linked silica aerogels can be found in US Patent Publication No. 2004/0132846 (Title: "Methods and compositions for preparing silica aerogels", Inventors: Nicholas Leventis and Chariklia Leventis, Filing date: Aug. 18, 2003), the entire contents of which are incorporated herein by reference. To test the applicability of aerogels as hybrid composites, samples of aerogels were cut into approximately identical shapes and sizes, as shown in Table 1 below, made to absorb water, and placed in two different lysis buffer solution kits procured from Invitrogen© (Carlsbad, Calif.) and Agencourt Bioscience (Beverly, Mass.), as shown in Table 2. As shown in Table 3 below, each sample was rated on a scale of 1 to 5 in terms of increasing dissolution and recovery of the buffer solution. Subsequently, each sample was tested for the bead capture, and rated on a scale of 1 to 5, as shown in Table 4 below.

TABLE 1

| Chemical Composition: | Swab-1 | Swab-2 | Swab-3 | Swab-4 |
|---|---|---|---|---|
| TMOS | 2.5 | 2.5 | 2.5 | 2.5 |
| APTS | — | 0.589 | 0.587 | — |
| MAPTS | 0.815 | — | — | 0.815 |
| DI $H_2O$ | 0.840 | 0.840 | 0.840 | 0.840 |
| $NH_4OH$ | 0.577 | 0.577 | 0.577 | 0.577 |
| Methanol | 6.630 | 6.178 | 6.178 | 6.630 |
| PEG | 0.331 | 0.331 | — | — |
| $NaHCO_3$ | 0.085 | 0.085 | 0.085 | 0.085 |
| Amount of Water Absorbed (μl) | 300 | 300 | 300 | 300 |

TABLE 2

| Kit | Lysis Buffer | Proteinase K | Lysis conditions |
|---|---|---|---|
| Invitrogen | 1 ml | 10 μl | 60° C. for 15 min |
| Agencourt | 0.8 ml | 18 μl (96 μg/ml) | 37° C. for 10 min |

TABLE 3

| Lysis Buffer Kit | Swab-1 | Swab-2 | Swab-3 | Swab-4 |
|---|---|---|---|---|
| Invitrogen | 2 | 3 | 3 | 3 |
| Agencourt | 2 | 1 | 1 | 2 |

TABLE 4

| Lysis Buffer Kit | Swab-1 | Swab-2 | Swab-3 | Swab-4 |
|---|---|---|---|---|
| Invitrogen | 2 | 3 | 4 | 3 |

Subsequently, the gel solution 225 can be subjected to a gelation process where, due to condensation and polymerization, the gel solution 225 solidifies into the inorganic portion of the hybrid composite 105 that has a porous structure. In some implementations, the gelation process can include leaving the gel solution 225 in ambient temperature for a pre-determined period of time, for example, 24 hours. Alternatively, gelation can include subjecting the gel solution 225 to temperature, pressure, or both. The choice of precursors 205 and other components of the hybrid composite 105 can affect gelation time. In some implementations, the gel solution 225 can be poured into pre-shaped molds so that the shape of the resulting hybrid composite 105 can be suitable for sample collection. For example, the gel solution 225 can be poured into a mold and the base 120 can be positioned in the mold with a portion of the base 120 immersed in the gel solution 225. Gelation can cause the hybrid composite 105 to be affixed to the base 120.

The porous structure of the inorganic portion of the hybrid composite 105 can contain a solvent that can be the polymerization solution 215. The hybrid composite 105 can be formed by removing the solvent from within the porous structure of the hybrid composite 105, thereby replacing the solvent with air. In some implementations, the hybrid composite 105 can be dried under ambient conditions. The solvents can evaporate from within the pores of the hybrid composite 105. In other implementations, the hybrid composite 105 can be treated to remove the solvents from the porous structure, for example, subjecting the hybrid composite 105 to temperature, pressure, or both. In other implementations, the hybrid composite 105 can be super-critically dried under high pressure and temperature. In some implementations, the solvent in the porous structure may be unsuitable for high pressure and temperature processing. For example, if the solvent is water, then drying may weaken the hybrid composite 105 structure or cause the structure to collapse. In such implementations, the solvent in the pores can be exchanged with a solvent, for example, acetone, acetonitrile, tetrahydrofuran, and the like, that can easily be removed from the pores. Also, the solvent used during solvent exchange can include additional polymers with which the hybrid composite 105 can be treated to further increase the structural rigidity of the hybrid composite 105.

Subsequent to forming the inorganic portion of the hybrid composite 105, a polymer, for example, MMA, can be attached to the surface. The functional property provided to the surface of the inorganic portion of the hybrid composite 105 due to the addition of the alkoxy silane can enable attaching the MMA to the surface of the hybrid composite 105. The MMA monomers can be polymerized to form a layer of pMMA which can be attached to the surface of the hybrid composite 105 by, for example, double bonds imparted to the surface by the alkoxy silane.

In some implementations, the hybrid composite 105 can be molded in the form of the tip of a cotton swab where the base 110 is a thin plastic rod with the hybrid composite 105 attached to one end. The gel solution 225 can be prepared and poured into a mold and the base 110 can be inserted into the mold. In this manner, the resulting hybrid composite 105 can be attached to the end of the base 110. Subsequently, the hybrid composite 105 can be dried or alternatively, molded into any size, shape, or form. In some implementations, sample can be collected by placing the hybrid composite 105 attached to the base 110 against the sample. For example, the sample can be biological cells in saliva. The cells can contain DNA. When the hybrid composite 105 is placed against the saliva, the cells in the saliva can adhere to the surface of the hybrid composite 105. Alternatively, or in addition, the cells in the saliva can be absorbed into the hybrid composite 105.

In some implementations, adhesion can be due to mechanical forces including entrapment in the porous structure of the hybrid composite 105, absorption, adsorption, capillary action, and the like. For example, the pores of the hybrid composite 105 can be manipulated using appropriate components in the gel solution 225 such that when the hybrid composite 105 is placed against the sample, the sample is entrapped in the pores. In other implementations, the hybrid composite 105 can be swiped against the sample. The high surface area properties of the hybrid composite 105 can be utilized to attach samples to the hybrid composite 105. In other implementations, the sample can be placed in contact with the hybrid composite 105. For example, the sample can be a drop of blood collected from a donor. The skin of the donor can be punctured and the donor's blood can be dropped on the surface of the hybrid composite 105. The impact of the blood drop on the hybrid composite 105 surface can cause entrapment of the blood in the porous structure of the hybrid composite 105. In this manner, samples can be attached to the surface of the hybrid composite 105.

Once the sample is attached to the hybrid composite 105, the hybrid composite 105 and the sample can be exposed to an appropriate liquid medium 115 to separate the hybrid composite 105 and the sample. In some implementations, the sample can be attached to the hybrid composite 105 under controlled experimental conditions. For example, the sample can be found on a biological tissue in a laboratory. The hybrid composite 105, attached to the end of a base, can be swiped against the biological tissue to collect the samples. In such implementations, a liquid medium may be immediately available so that a user can expose the hybrid composite 105 with the sample to the medium. In other implementations, the sample can be found in an uncontrolled environment, for example, in a crime scene as a blood splatter. A user can attach the hybrid composite 105 to the blood splatter and transport the hybrid composite 105 with the sample to a laboratory for further processing. In other implementations, the aerogel with the attached sample can be stored under appropriate conditions, for example, low temperatures such as −20° C., such that the sample can be separated from the hybrid composite 105 at any point in time.

In some implementations, the liquid medium 115 can be located in a container, for example, a beaker, a test tube, a Petri dish, and the like. The hybrid composite 105 with the attached sample can be immersed into the liquid medium 115 which can be a strong acid, weak acid, strong base, weak base, organic solvents, water, and the like, that can be tailored to not only separate the sample from the hybrid composite 105, but also to not destroy the hybrid composite 105. In addition, the liquid medium 115 can be tailored to prepare the sample for subsequent processing. For example, if the sample contains deoxyribonucleic acid (DNA) to be analyzed, the liquid medium 115 can separate the sample from the hybrid composite 105, and lyse the sample to enable access to the DNA. The solvent can be chosen based on its properties to separate the sample from the hybrid composite 105. Alternatively, the properties can be manipulated to enable separating the sample from the hybrid composite 105.

In some implementations, the liquid medium 115 can degrade the surface of the hybrid composite 105 and increase the pore size, thereby releasing the sample from the porous structure of the aerogel. In other implementations, the solvent can dissolve all the aerogel leaving only the released samples. The same liquid medium 115 can be used to either dissolve the entire hybrid composite 105 or degrade only the surface of the hybrid composite 105. For example, the hybrid composite 105 with the attached sample can be immersed into the liquid medium 115 for a pre-determined period of time. Within this period, only the surface of the hybrid composite 105 can be degraded. Prolonged immersion in the liquid medium 115 can cause complete dissolving of the hybrid composite 105. In addition, the liquid medium 115 can be chosen based on the biocompatibility properties of the liquid medium 115 whereby the properties of the sample remain intact and are not rendered unsatisfactory for further processing, once the sample is released from the hybrid composite 105 surface into the medium 115.

In some implementations, the liquid medium 115 used to separate the samples from the hybrid composite 105 can be flowed onto the hybrid composite 105. The samples can be separated from the hybrid composite 105 and flowed with the liquid medium 115 into a container where the samples can be collected. In other implementations, the liquid medium 115 can be sprayed on the hybrid composite 105. In some implementations, the hybrid composite 105 with the attached sample can be positioned in a microfluidic channel fabricated on a microfluidic device. The liquid medium 115 can be flowed through the microfluidic device over the hybrid composite 105. The samples can be separated from the hybrid composite 105 and flowed into a chamber designed to collect samples.

FIG. 3 is a flow chart of an example of a process 300 for collecting samples using a porous substrate. A hybrid composite 105 is brought in contact with a biological sample to attach the biological sample to the aerogel at 305. The hybrid composite 105 can be prepared by dispersing an alkoxy silane in an inorganic porous matrix to provide functional properties to the inorganic matrix including the surface of the matrix. Subsequently, an organic polymer layer can be attached to the surface of the inorganic matrix, by virtue of the surface functionality imparted to the matrix by the alkoxy silane, to prepare hybrid composite 105. The sample can be a biological sample containing DNA. Mechanical forces, for example, entrapment in the porous structure, absorption, adsorption, capillary action, and the like, can cause the biological sample to attach to the hybrid composite 105. Alternatively, the sample can be attached to the hybrid composite 105 by chemical forces.

The hybrid composite 105 with the attached sample can be placed in a medium at 310 to separate the sample from the hybrid composite 105. The medium can be chosen based on its properties to separate the sample from the hybrid composite 105. Alternatively, or in addition, the properties of the medium can be altered to enable separating the samples from the hybrid composite 105. In some implementations, the medium can degrade the surface of the hybrid composite 105, thereby causing the attached samples to be released. In other implementations, the medium can dissolve the entire hybrid composite 105, thereby causing the attached samples to be released. In some implementations, the samples can be entrapped in the pores of the hybrid composite 105. The medium can cause the pores of the hybrid composite 105 to enlarge, thereby causing the entrapped sample to be released. In some implementations, the sample can be attached to the hybrid composite 105 by chemical forces. When the hybrid composite 105 with the attached sample is placed in the medium, the medium can cause reversal of the chemical forces that hold the sample to the hybrid composite 105. For example, the attraction between the medium and the sample can be greater than that between the sample and the hybrid composite 105. Thus, the sample can be detached from the hybrid composite 105.

In some implementations, the surface of the hybrid composite 105 can be treated to be a pre-determined value causing the sample to be attached to the hybrid composite 105. For example, the pH of the medium in which the hybrid composite 105 and the sample are placed can be chosen such that the sample is driven away from the hybrid composite 105 and into the medium, thereby separating the sample from the hybrid composite 105. The separated sample can be collected in the medium at 315. In some implementations, the separated sample can be subsequently transferred from the medium to a different environment. In other implementations, subsequent to separating the sample from the hybrid composite 105, additional elements can be added to the medium to process the sample. For example, if the sample is a cell containing DNA, lysing agents can be added to the medium to break open the cell surface to allow access to the DNA. In other implementations, the medium can be chosen such that, in addition to separating the sample from the hybrid composite 105, the medium can additionally process the sample.

Figure 4:
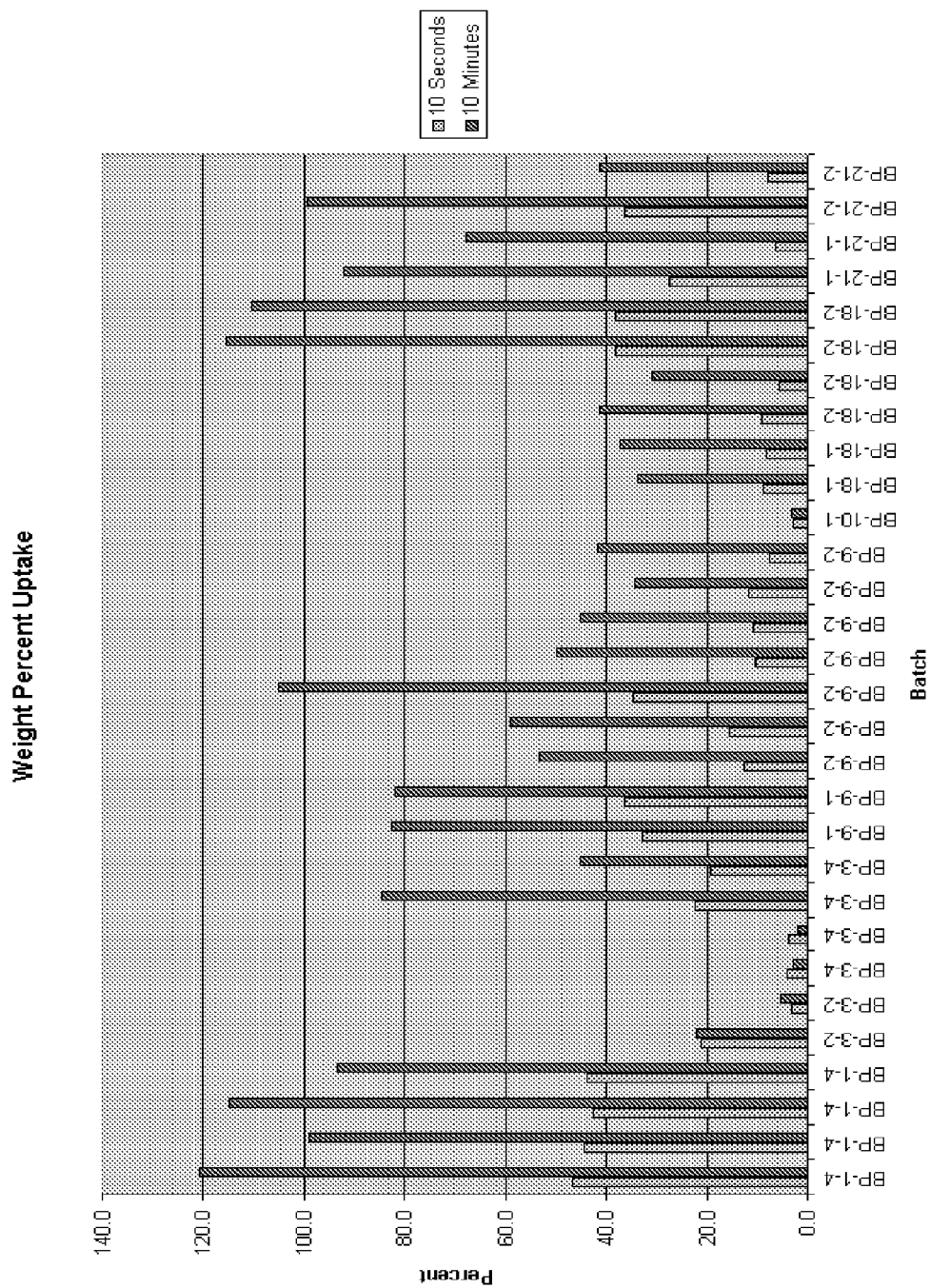
FIG. 4 is a graph of the water intake capability of cross-linked aerogels.
Figures 5A, 5B:
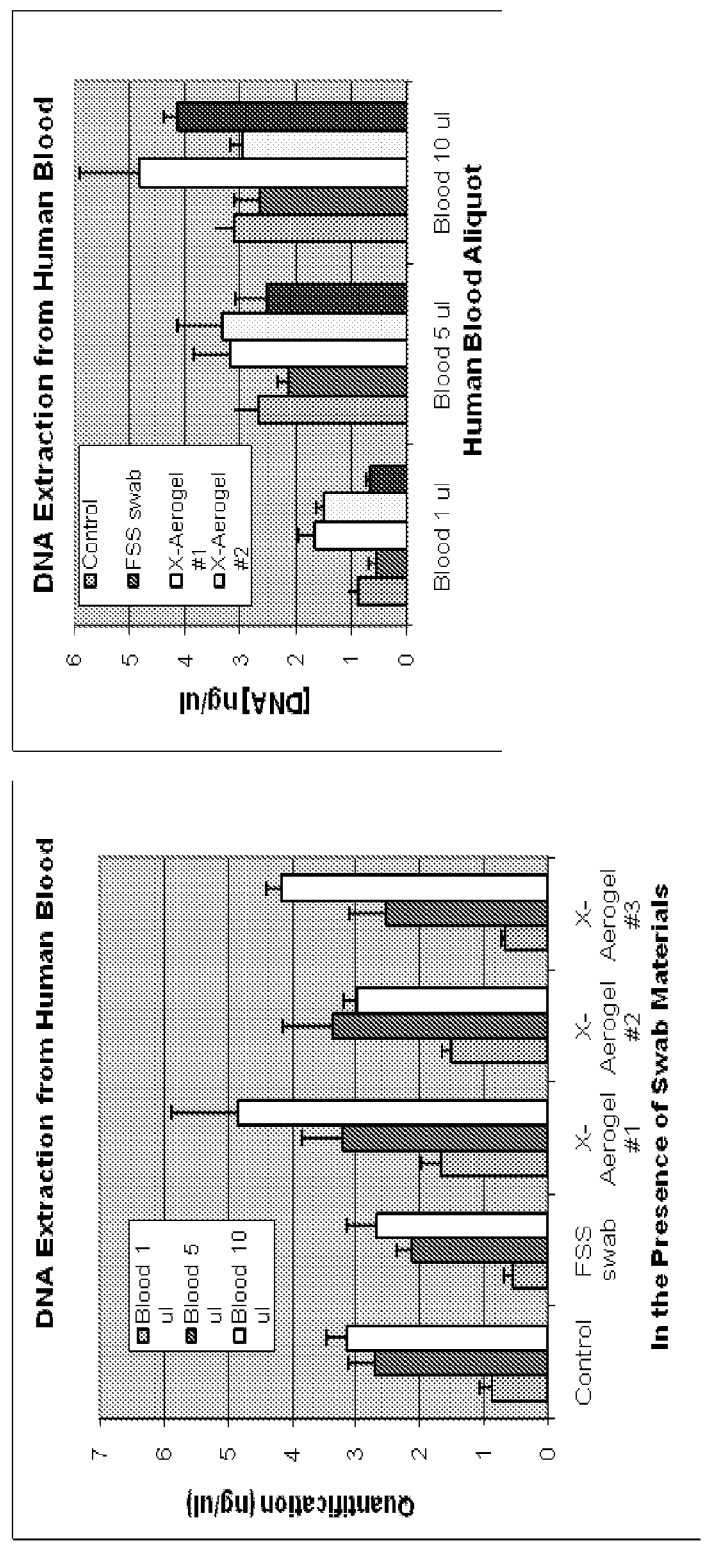
FIGS. 5A-5D show graphs depicting the extraction efficiency of human gDNA when aerogels are used as hybrid composites.
Figures 5C, 5D:
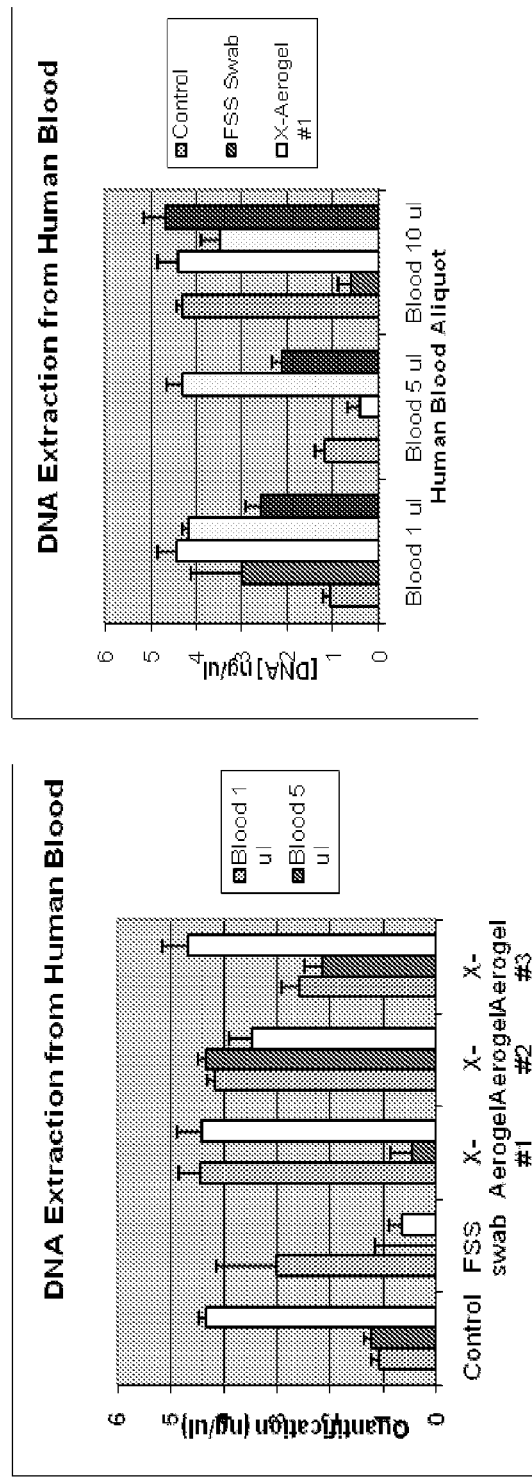

FIG. 4 is a graph depicting the percent water intake of a batch of inorganic organic hybrid composites, for example, cross-linked aerogels. In some implementations, the cross-linked aerogels can be cross-linked with MMA. PEG, with molecular weight varying between 1,000 and 10,000, can be included in the sol-gel. The PEG can be extracted out of the cross-linked aerogel leaving behind relatively large pores. Linear PEG can be used in making the cross-linked aerogels. However, other forms of PEG, for example, tri-block PEG, can also be used to modify the pore size. As can be seen in FIG. 4, the cross-linked aerogel samples absorb a considerable amount of water without decomposition, for example, more than 100% water. For example, aerogel having weight in the range of 0.12 g to 0.15 g can absorb approximately 300 µL of water. The water uptake was measured at 10 s and 10 minutes after immersion. The cross-linked aerogels were dried at ambient conditions. The graph, illustrated in FIG. 4, indicates that the cross-linked aerogels can be immersed in a liquid medium, such as water, without the degrading of the cross-linked aerogel structure. This suggests that if a cross-linked aerogel is used to collect sample, the aerogel with the attached sample can be stored in a liquid medium without the cross-linked aerogel degrading.

FIGS. 5A-5D show graphs depicting the extraction efficiency of human gDNA when aerogels are used as hybrid composites. Three types of aerogel samples, a control sample with no aerogel, and a sample known to attach to gDNA were tested. The efficiency of the samples to extract DNA from human blood is shown in FIGS. 5A-5D.

While this document contains many specifics, these should not be construed as limitations on the scope of the specification or of what may be claimed, but rather as descriptions of features specific to particular implementations of the document. Certain features that are described in this document in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

For example, the inorganic portion of the hybrid composite can be an aerogel. Aerogels comprise a unique class of materials that are chemically similar to glass. Microscopically, aerogels consist of a three dimensional pearl-necklace like network of nanoparticles giving the aerogels a porous microstructure. As a result, aerogels can consist mostly of empty space (as high as 95%-99.9%), and can be characterized by low density (as low as 0.003 g/cc) and high surface area (as high as 1000 $m^2$/g). The sample can be attached to the aerogel by chemical adhesion, for example, covalent bonding, Van der Waals forces, and the like.

For example, polymers, such as PMMA, can be grown on the surface of the aerogel, where the polymers can be sensitive to solvents such as acids, bases, water, organic solvents, and the like. By choosing an appropriate solvent, the polymer can be degraded causing the decomposition of the aerogel to release the attached sample.

The hybrid composite can be of various sizes, shapes, or forms. In some implementations, the hybrid composite can be machined into any desired shape. For example, the hybrid composite can be machined in the form of a flat surface. The flat surface can be placed on the sample to enable the sample to attach to the surface of the hybrid composite. In some implementations, the sample may be spread out over a large area. In such implementations, the hybrid composite can be stored as an aerosol and sprayed over the area over which the sample is spread. Subsequently, the hybrid composite spray with the attached samples can be collected for further processing.

In some implementations, the sample attached to the hybrid composite can be separated shortly after collecting the samples. In other implementations, the hybrid composite with the attached sample can be stored for an extended period of time. Such storage can be under ambient conditions or under controlled conditions, where the conditions can include temperature, pressure, humidity, and the like. In such implementations, the properties of the hybrid composite can be manipulated to remain stable over time and remain unaffected by the conditions under which the hybrid composite is stored. In other implementations, experiments can be conducted to determine an age for the hybrid composite, for example, a time beyond which the hybrid composite degrades. Such experiments can include surface area measurements, density measurements, surface chemistry tests, and the like. Based on the determined age of the hybrid composite, a sample can be transferred from an old hybrid composite substrate to a new hybrid composite substrate prior to expiry of the age of the old hybrid composite. For example, the sample can be transferred from the old hybrid composite to the medium, the medium can be evaporated leaving only the sample, and the sample can be collected using the new hybrid composite for further storage.

In some implementations, the hybrid composite with the attached sample can be immersed into the liquid medium and subjected to mechanical forces by methods such as ultrasound. The forces due to the ultrasound can release the samples from the hybrid composite substrate without destroying the sample.

In some implementations, the medium in which the sample is separated from the hybrid composite can be designed to further process the sample, for example, lyse the sample to enable access to the DNA in the sample. In some implementations, the hybrid composite can be embedded with functional agents that enable processing the sample at the site of collection. For example, the aerogels can be embedded with lysing agents and dyes for DNA detection. When the sample is collected using the hybrid composite, the sample can be lysed, and the DNA detection dye can be mixed with the DNA in the sample. The presence or absence of DNA can be indicated by the result of the mixing, for example, fluorescence output detected using optical spectroscopic instruments.

In other implementations, the hybrid composite can be sprayed on the sample in the form of an aerosol. Subsequent to lysing, the output of the mixing of the DNA detection dyes and the sample can enable identifying the location of sample. In some implementations, the samples can include pharmaceutical agents, microbials, and the like. In some implementations, the sample can be attached to porous nano-composite materials with functionalized surfaces. The materials with which the nano-composite materials are made can be chosen based on their sample adhesion properties.

Only a few implementations are described and illustrated. Variations, enhancements and improvements of the described implementations and other implementations can be made based on what is described and illustrated in this document.

What is claimed is:

1. A method for sample collection comprising:

contacting a hybrid porous material and a biological sample to the porous material, wherein the hybrid porous material includes an inorganic material and an organic material;

placing the porous material with the attached sample in a liquid medium, wherein the sample is separated from the porous material in the liquid medium to form a separated sample; and collecting the separated sample in the medium.

2. The method of claim 1, wherein the biological sample comprises deoxyribonucleic acid.

3. The method of claim 1, wherein placing the porous material with the attached sample in a liquid medium causes the porous material to dissolve in the liquid medium, thereby separating the sample.

4. The method of claim 1, wherein the hybrid porous material includes comprises a silane component, an alkoxy silane component, and an organic polymer component.

5. The method of claim 1, wherein the hybrid porous material consists of a silane component and an organic polymer component.

6. The method of claim 5, wherein the organic polymer component is attached to the surface of the inorganic organic hybrid composite material.

7. The method of claim 1, further comprising entrapping the biological sample in a porous structure of the porous material.

8. The method of claim 1, further comprising processing the porous material to chemically activate a surface of the porous material.

9. The method of claim 8, wherein contacting the porous material and the biological sample further comprises causing the biological sample to chemically adhere to the chemically activated surface.

10. The method of claim 1, wherein contacting the porous material and the biological sample further comprises placing the porous material on the biological sample.

11. The method of claim 1, wherein contacting the porous material and the biological sample further comprises swiping the porous material against the biological sample.

12. A method comprising:
attaching an inorganic material and an organic material, wherein a biological sample is attachable to the inorganic material and the attached organic material; and
collecting the biological sample with the inorganic material.

13. The method of claim 12, wherein collecting the biological sample with the inorganic material comprises:
attaching the biological sample to the inorganic material;
placing the inorganic material with the attached biological sample in a liquid medium to separate the biological sample from the surface; and
collecting the separated biological sample in the liquid medium.

14. The method of claim 13, wherein the biological sample is attached to a surface of the inorganic material.

15. The method of claim 13, wherein the biological sample is absorbed into an interior of the inorganic material.

16. The method of claim 12, wherein preparing the inorganic material to attach to the organic material comprises preparing the inorganic material by mixing a quantity of a silane, a quantity of an alkoxy silane, and a quantity of a solution, wherein the alkoxy silane prepares the inorganic material to attach to the organic material.

17. The method of claim 16, wherein the siloxane is tetramethylorthosilicate (TMOS).

18. The method of claim 16, wherein the solution comprises at least one of an alcohol and water.

19. The method of claim 18, wherein the alcohol is methanol.

20. The method of claim 18, wherein the solution comprises alcohol and water in a weight/volume ratio.

21. The method of claim 18, wherein the alkoxy silane is allyltrimethoxysilane.

22. The method of claim 16 wherein the organic material is polymethylmethacrylate (PMMA), wherein the PMMA is formed by polymerization of methyl methacrylate (MMA), and wherein the PMMA grows on the surface of the first material.

23. A system comprising:
a hybrid porous material including an inorganic material and an organic material, the hybrid porous material including a surface attachable to a biological sample; and
a liquid medium in which the biological sample separates from the surface.

24. The system of claim 23, wherein the hybrid porous material comprises a silane component, an alkoxy silane component, and an organic polymer component.

25. The system of claim 24, wherein the hybrid porous material is prepared by mixing a known quantity of the siloxane component, a known quantity of the alkoxy silane component, and a known quantity of a solution.

26. The system of claim 25, wherein the silane component is tetramethylorthosilicate (TMOS).

27. The system of claim 25, wherein the solution comprises at least one of an alcohol and water.

28. The system of claim 27, wherein the alcohol is methanol.

29. A method of manufacturing a hybrid composite, the method comprising:
adding an alkoxy silane to a precursor including a metal oxide to cause hydrolysis and condensation reactions;
adding a polymerization solution to the alkoxy silane and the precursor to cause a polymerization reaction to form a porous inorganic material; and
adding an organic functional component to the porous inorganic material wherein the organic component polymerizes and attaches to the porous inorganic material to form a hybrid composite, wherein the alkoxy silane, the precursor, the polymerization solution, and the organic functional component are selected such that a biological sample, when contacted by the hybrid composite, attaches to the hybrid composite.

30. The method of claim 29, wherein the metal oxide is based on one of silica, aluminum, vanadium, and ruthenium.

31. The method of claim 29, wherein the alkoxy silane is one of or a mixture of allyltrimethoxysilane, tetraethylorthosilicate, or tetramethylorthosilicate.

32. The method of claim 29, wherein the polymerization solution includes an alcohol.

33. The method of claim 32, wherein the polymerization solution additionally includes water.

34. The method of claim 32, wherein the alcohol is one of methanol and ethanol.

35. The method of claim 29, further comprising adding a catalyst to increase a rate of polymerization, the catalyst including one or hydrochloric acid, nitric acid, and sodium hydroxide.

36. The method of claim 29, wherein the organic functional component is methylmethacrylate.

37. The method of claim 29, further comprising attaching the hybrid composite to a rod.

38. An apparatus comprising:
a hybrid porous material including an inorganic material and an organic material, the hybrid porous material manufactured using an alkoxy silane, a precursor having a metal oxide mixed with the alkoxy silane, a polymerization solution to polymerize the alkoxy silane mixed with the precursor, and an organic functional component included in the organic material, wherein the alkoxy silane, the precursor, the polymerization solution, and the organic functional component are selected such that a biological sample, when contacted by the hybrid porous material, attaches to the hybrid porous material; and
a rod having an end attached to the hybrid porous material, wherein the porous material attached to the rod is swiped against the biological material so that the hybrid porous material contacts the biological sample.

39. The system of claim 38, wherein the alkoxy silane is tetramethylorthosilicate (TMOS).

40. The system of claim 38, wherein the polymerization solution comprises at least one of an alcohol and water.

41. The system of claim 40, wherein the alcohol is methanol.

42. A hybrid composite material manufactured by a method comprising:
- adding an alkoxy silane to a precursor including a metal oxide to cause hydrolysis and condensation reactions;
- adding a polymerization solution to the alkoxy silane and the precursor to cause a polymerization reaction to form a porous inorganic material; and
- adding an organic functional component to the porous inorganic material wherein the organic component polymerizes and attaches to the porous inorganic material to form the hybrid composite, wherein the alkoxy silane, the precursor, the polymerization solution, and the organic functional component are selected such that a biological sample, when contacted by the hybrid composite, attaches to the hybrid composite.

43. The hybrid composite material of claim 42, wherein the metal oxide is based on one of silica, aluminum, vanadium, and ruthenium.

44. The hybrid composite material of claim 42, wherein the alkoxy silane is one of or a mixture of allyltrimethoxysilane, tetraethylorthosilicate, or tetramethylorthosilicate.

* * * * *